(12) United States Patent
Allmendinger et al.

(10) Patent No.: US 8,699,772 B2
(45) Date of Patent: Apr. 15, 2014

(54) SCANNING OF A CYCLICALLY MOVED EXAMINATION OBJECT USING A CONTRAST AGENT WITHIN THE SCOPE OF A PRELIMINARY EXAMINATION BY MEANS OF A CT SCANNER

(75) Inventors: Thomas Allmendinger, Forchheim (DE); Jörg Hausleiter, München (DE); Heiko Mehldau, Nürnberg (DE); Carsten Thierfelder, Pinzberg (DE)

(73) Assignee: Siemens Aktiengesellschaft, Munich (DE)

( * ) Notice: Subject to any disclaimer, the term of this patent is extended or adjusted under 35 U.S.C. 154(b) by 371 days.

(21) Appl. No.: 12/892,011

(22) Filed: Sep. 28, 2010

(65) Prior Publication Data

US 2011/0075906 A1    Mar. 31, 2011

(30) Foreign Application Priority Data

Sep. 29, 2009  (DE) .......................... 10 2009 043 633

(51) Int. Cl.
*G06K 9/00*          (2006.01)
(52) U.S. Cl.
USPC .......................................... 382/131; 382/128
(58) Field of Classification Search
None
See application file for complete search history.

(56) References Cited

U.S. PATENT DOCUMENTS

| | | | |
|---|---|---|---|
| 6,243,437 B1 * | 6/2001 | Hu et al. ............................ | 378/8 |
| 6,535,570 B2 * | 3/2003 | Stergiopoulos et al. .......... | 378/8 |
| 6,708,052 B1 * | 3/2004 | Mao et al. ...................... | 600/407 |
| 7,181,054 B2 | 2/2007 | Zaleski | |
| 7,539,529 B2 * | 5/2009 | Schmitt et al. ................. | 600/431 |
| 8,422,625 B2 * | 4/2013 | Bruder et al. ....................... | 378/8 |
| 2003/0048932 A1 * | 3/2003 | Zaleski .......................... | 382/128 |
| 2003/0161435 A1 * | 8/2003 | Ozaki ............................... | 378/4 |
| 2004/0179644 A1 * | 9/2004 | Tsuyuki ............................. | 378/8 |
| 2006/0133564 A1 * | 6/2006 | Langan et al. .................... | 378/8 |
| 2006/0210134 A1 * | 9/2006 | Grass et al. .................... | 382/130 |
| 2007/0009080 A1 * | 1/2007 | Mistretta ........................... | 378/4 |
| 2007/0030946 A1 * | 2/2007 | Tsuyuki et al. .................... | 378/8 |
| 2007/0032735 A1 * | 2/2007 | Bruder et al. ................. | 600/523 |

(Continued)

FOREIGN PATENT DOCUMENTS

| | | |
|---|---|---|
| CN | 1907227 A | 2/2007 |
| DE | 102007053390 A1 | 12/2008 |

OTHER PUBLICATIONS

German OA dated Jun. 23, 2010.

*Primary Examiner* — Stephen R Koziol
*Assistant Examiner* — Sean Conner
(74) *Attorney, Agent, or Firm* — Harness, Dickey & Pierce (57) ABSTRACT

A method is disclosed for scanning a cyclically moved examination object using a contrast agent within the scope of a preliminary examination by way of a CT scanner, in which measurement data is recorded at a sequence of recording times. A first image is reconstructed at every recording time from the measurement data, from which a time profile of a concentration of the contrast agent is established. The recording times for respectively recording a certain phase of the motion are synchronized with a motion signal from the examination object. A second image with a time offset with respect to the first image is reconstructed from the measurement data at each recording time. A motion curve representing a time profile of an intensity of the cyclical motion is established by comparing the first image and the second image at each recording time.

13 Claims, 2 Drawing Sheets

(56) References Cited

U.S. PATENT DOCUMENTS

| | | | |
|---|---|---|---|
| 2007/0140411 A1* | 6/2007 | Manzke et al. | 378/8 |
| 2007/0237286 A1* | 10/2007 | Imai | 378/4 |
| 2008/0100617 A1* | 5/2008 | Keller et al. | 345/421 |
| 2008/0170654 A1* | 7/2008 | Tkaczyk et al. | 378/8 |
| 2008/0253505 A1* | 10/2008 | Imai | 378/8 |
| 2011/0081068 A1* | 4/2011 | Brinks et al. | 382/132 |
| 2011/0164800 A1* | 7/2011 | Kokubun | 382/131 |
| 2011/0293155 A1* | 12/2011 | Nakanishi et al. | 382/131 |

* cited by examiner

FIG 1

SCANNING OF A CYCLICALLY MOVED EXAMINATION OBJECT USING A CONTRAST AGENT WITHIN THE SCOPE OF A PRELIMINARY EXAMINATION BY MEANS OF A CT SCANNER

PRIORITY STATEMENT

The present application hereby claims priority under 35 U.S.C. §119 on German patent application number DE 10 2009 043 633.2 filed Sep. 29, 2009, the entire contents of which are hereby incorporated herein by reference.

BACKGROUND

Methods for scanning an examination object using a CT scanner are well known. Therein, use is made of e.g. circular scans, sequential circular scans with feed, or helical scans. In these scans, at least one X-ray source and at least one opposing detector are used to collect measurement data in the form of absorption data from the examination object over an angular interval, and this data is operated on by way of appropriate reconstruction methods to form images, e.g. slice images.

These days, a so-called filtered back projection (FBP) method is used as a standard method for reconstructing the images. After the data acquisition, a so-called "rebinning" step is performed, in which the measurement data generated by the beam expanding in a fan-like fashion from the source is reordered such that it is available in a form as if the detector was hit by beams running parallel toward the detector. The measurement data is then transformed into the frequency space. Filtering takes place in the frequency space and the filtered data is subsequently subjected to an inverse transform. Using the measurement data resorted and filtered in this fashion, a back projection onto the individual voxels within the region of interest is then carried out.

A disadvantage in scanning an examination object subjected to or undergoing cyclical motion, for example a heart or a lung or an examination object at least partly subjected to cyclical motion, consists of the fact that motion unsharpness can be generated in the images in these calculation methods. This is because there can be, as a function of the recorded intensity of the motion, a spatial offset of the examination object or part of the examination object in the measurement data, which is recorded during the time of a scanning procedure and required for reconstructing the image, and so not all of the measurement data reflects spatially identical situations of the examination object. This motion unsharpness problem is particularly amplified when carrying out cardiac CT examinations of a patient, in which there is strong motion unsharpness in the cardiac region due to the cardiac motion.

In order to avoid such motion unsharpness, the measurement data is therefore recorded whilst evaluating a motion signal; in the case of the heart this is whilst evaluating an EKG signal transferred from the patient. Two reconstruction methods exist, which in principle differ in terms of their approach.

In the case of retrospective reconstruction, measurement data is recorded over the entire cycle duration of the cardiac motion and stored together with the EKG signal. An image is reconstructed retrospectively, following data acquisition, wherein measurement data of rest phases of the heart is selected either by evaluating the EKG signal or by evaluating the motion information contained in the data records using a well-known motion-mapping method. An advantage consists of the fact that the rest phases of the heart can be determined individually for each cycle, and so the reconstructed image has few motion artifacts. However, a requirement for the retrospective reconstruction of an image is that the patient is irradiated with the full X-ray dose throughout the entire scan, and so a significantly higher X-ray dose than necessary is applied. That is to say measurement data that is not required for the actual reconstruction is also recorded during the scan.

In the case of prospective reconstruction, a recording time for a temporally subsequent phase of the cardiac motion to be scanned is estimated on the basis of a registered R-wave and an established RR-interval duration. In the process, the R-wave of the EKG signal is used as a trigger to start the scanning after a delay predefined by the recording time. Thus, the recording time is the time interval between the registered R-wave and the start of measurement data acquisition within the subsequent motion cycle. It can selectively be specified in relation to the established RR-interval duration, e.g. in percent, or else in time units. The recording time in general is fixed by an operator using their experience and as a function of the observed characteristic in the EKG profile. A particular disadvantage of this is that the result of the image reconstruction depends strongly on the experience of the respective operator. Thus, what can occur is that the predefined recording time does not coincide with the phase or the rest phase of the cardiac motion in an optimum fashion, leading to a reduction in the obtainable image quality. However, an advantage of prospective reconstruction of tomographic images can be seen in the fact that the tube current is modulated such that the X-ray dose is only applied during a short time interval.

A further aspect increasing the difficulty of scanning is the fact that the cyclically moved examination objects in the patient, namely the heart or the lung, have attenuation properties similar to their surroundings, and so they are imaged with only little contrast in the image if no further measures are taken. It is for this reason that a contrast agent is injected into the patient before the examination is started. Compared to the surrounding tissue, the contrast agent has a different attenuation property, and so a significant contrast is generated in the image between the examination object and the surroundings.

The diffusion of the contrast agent in the body of the patient is a highly dynamic process. The concentration of the contrast agent in the examination object first of all increases sharply after a certain time delay, reaches a maximum, and subsequently falls off again. So that data is recorded at the right time, namely at the time of maximum concentration of the contrast agent in the examination object, a preliminary examination with a small amount of the contrast agent (test bolus) is first of all carried out at the beginning of each examination and the goal thereof is to establish the time profile of the contrast-agent concentration or the contrast-agent curve.

In the process, measurement data is recorded at a sequence of recording times, wherein a first image is reconstructed from the measurement data at each recording time and the images are used to establish a time profile of a concentration of the contrast agent.

In cardiac CT examinations, measurement data is recorded for example in the upper cardiac region of the ascending aorta at a fixedly predefined time interval, for example in a one-second interval. A slice image is reconstructed from the measurement data at each recording time. The time profile of the contrast agent concentration is subsequently established from the profile of the attenuation values from a ROI positioned in the slice images in the region of the aorta. The number of required scans depends individually on the patient and varies between 3 and 15.

SUMMARY

In at least one embodiment of the invention, the preconditions for improved scanning of a cyclically moved examination object are developed, using a contrast agent by way of a CT scanner.

This is achieved by a method in at least one embodiment, and also by a CT scanner, a computer program and/or a computer program product. Advantageous refinements and developments are the subject matter of dependent claims.

The method according to at least one embodiment of the invention is a method carried out within the scope of a preliminary examination by way of a CT scanner for scanning a cyclically moved examination object using a contrast agent. In the process, measurement data is recorded at a sequence of recording times, with a first image being reconstructed at every recording time from the measurement data. A time profile of a concentration of the contrast agent is established from the first images. According to the invention, the recording times for respectively recording a certain phase of the motion are additionally synchronized with a motion signal from the examination object. Furthermore, a second image with a small time offset with respect to the first image is reconstructed from the measurement data at each recording time, wherein a motion curve representing a time profile of an intensity of the cyclical motion is established by comparing the first image and the second image at each recording time. By way of example, a heart or a lung is used as examination object and an EKG signal or a respiratory signal is used as motion signal.

Thus, the preliminary examination that is mandatory as a result of using a contrast agent is not only used, as previously, to establish the time profile of the contrast agent concentration, but also to establish the information relating to the intensity of the motion correlated to the motion signal. The time profile of the intensity of the motion over a cycle is specified by the motion curve. Scanning times at rest phases of the cyclical motion can subsequently be determined in an improved fashion from this motion curve. Hence high quality images, which have almost no motion artifacts, can be reconstructed. Thus, the experience of a medical practitioner is no longer required for selecting the correct scanning times, and so less experienced users can also carry out the examination.

More particularly, the inventors have recognized that the additional information in respect of the motion of the examination object can be obtained by a minor modification of the scanning protocol used in the preliminary examination. Namely, the scanning times are no longer arranged at a fixedly set time interval, as has been conventional until now. According to at least one embodiment of the invention, they are synchronized with the motion signal. As mentioned at the outset, an R-wave of the EKG signal is for example used as a trigger here to start the scan after a delay predefined by the recording time. The recording time is the time interval between the registered R-wave and the start of measurement data acquisition within the subsequent motion cycle. It can selectively be specified in relation to the established RR-interval duration, e.g. in percent, or else in time units. Moreover, the recording times are placed within a cycle such that different phases of the motion are recorded. Motions express themselves as displacements of the examination object in the images. Therefore, so much measurement data is collected at each recording time such that a second image can be reconstructed at a small time offset to the first image, with the motion information being obtained from comparing the images obtained in this fashion. Thus, the additional information relating to the motion can be generated within the scope of the preliminary examination with minimal additional dose.

In a refinement of at least one embodiment of the invention, the recording times are selected such that the recorded phases are arranged distributed as equidistantly as possible over a motion cycle at every observed time. That is to say the measurement data should cover the entire range between 0% and 100% of the cycle duration in an even fashion. Thus, it is not expedient for the sequence to start at 0% and be incremented in each case by a fixed percentage, e.g. 5%, because the number of scans is not fixed a priori and hence the optimum increment for even coverage cannot be determined.

It is advantageous if the sequence of recording times is determined from a van der Corput sequence with base two. This sequence fills a predefined interval as evenly as possible at all times and allows almost equidistant scanning.

In a development of at least one embodiment of the invention, a motion measured value is established as a measure of the intensity of the cyclical motion at each recording time from a difference between the first image and the second image. In the process, corresponding image data from the first and the second image is subtracted from each other pixel-by-pixel. By summing the absolute values of the differences formed thus and by normalizing the value of the sum in respect of the number of pixels and optionally by further normalizing this in respect of the observed maximum of the sum values normalized thus, a value results at each recording time and it is a measure of the motion of the examination object.

In a refinement of at least one embodiment of the invention, the motion curve is determined by approximating a model function to the established motion measured values at the recording times. In the process, the model function contains a priori knowledge relating to the motion profile, and so the motion curve can be determined with a small number of nodes, with each node being formed from the pair of values: recording time and intensity value of the motion. The approximation is advantageously undertaken using a chi-square fit based on the least-squares method.

In a development of at least one embodiment of the invention, at least one scanning time with little motion of the examination object is established and it corresponds to a local minimum of the motion curve. The motion artifacts in the reconstructed image are smallest at this scanning time.

A significance value is preferably established for this scanning time and this represents a measure of the probability of this minimum occurring. The size of the data interval for recording measurement data at the scanning times can be fixed on the basis of this information. If, in the case of a low probability being present, there is a high risk of not coinciding with the minimum of the motion or the rest phase of the cyclical motion, the data interval, which corresponds to the time interval in which measurement data is collected, can be selected to be so large that a retrospective reconstruction of the image is possible at the optimum phase.

The CT scanner according to at least one embodiment of the invention comprises a control and computational unit used for reconstructing images of the examination object from measurement data. It comprises a program storage medium for storing program code, wherein program code available (if necessary inter alia) in the program storage medium is suitable for executing a method of the aforementioned type. It can additionally contain other components that are required, for example for recording measurement data.

The computer program according to at least one embodiment of the invention has program-code segments available that are suitable for carrying out the method of the aforementioned type when the computer program is executed on a computer.

BRIEF DESCRIPTION OF THE DRAWINGS

Hereinbelow, the invention will be explained in more detail with the aid of an example embodiment and with the aid of schematic drawings, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
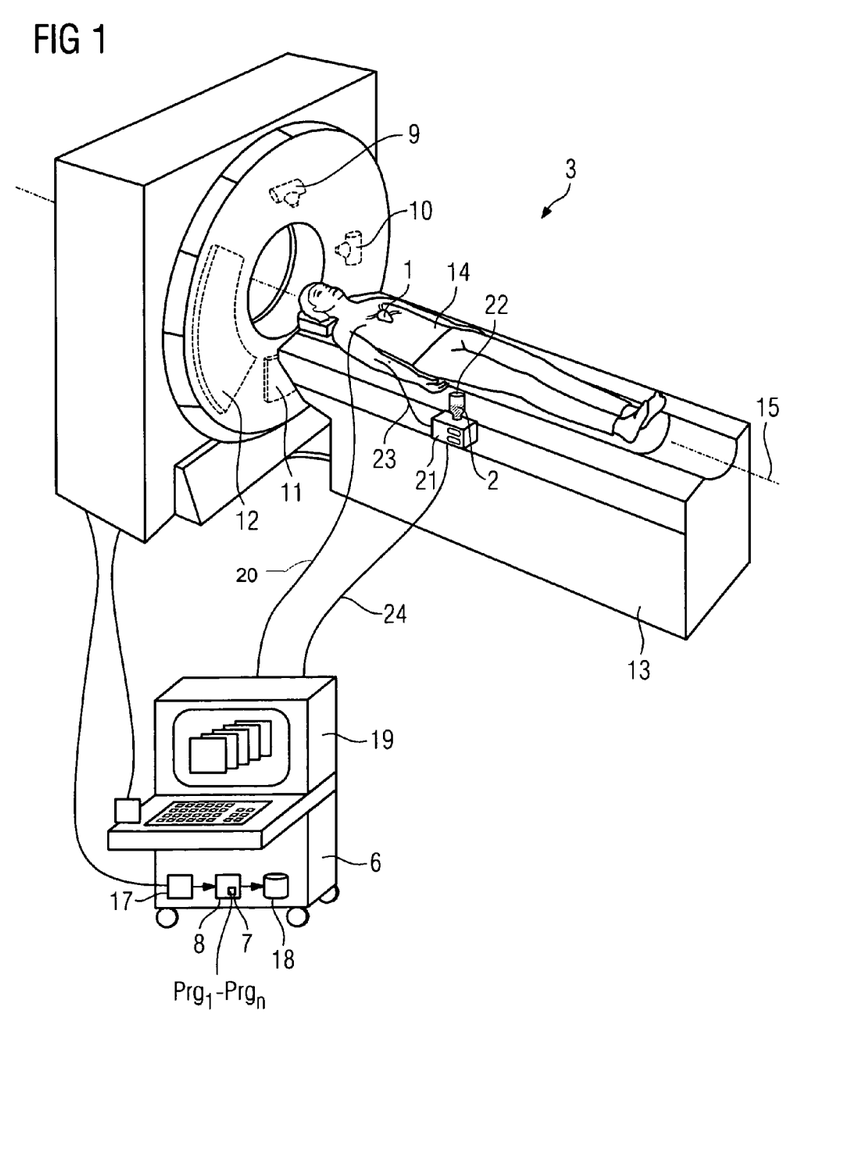
FIG. 1 shows a perspective view of a CT scanner with an image reconstruction component suitable for carrying out the method according to an embodiment of the invention.

FIG. 1 illustrates a CT scanner 3 in the form of a computed tomography system with an image reconstruction arrangement 8. In the gantry housing there is a closed gantry (not illustrated here), on which is arranged a first recording system 9, 11 comprising a first X-ray tube 9 with a first detector 11 arranged opposite it. The CT scanner 3 illustrated here optionally has a second recording system 10, 12 arranged therein, which second recording system is arranged offset to the first recording system 9, 11 by an angle of for example 90 degrees. The additional recording system 10, 12 affords the possibility of achieving a higher time resolution, or else dual-energy examinations can be carried out if different X-ray energy spectra are used in the recording systems 9, 11, 10, 12.

The CT scanner 3 furthermore comprises a patient couch 13, on which a patient 14 can be moved along a system axis 15, also referred to as z-axis, and into the measurement field during the examination, wherein the scan itself can also take place as a purely circular scan, only in the examination region of interest, without the patient being advanced. In the process, the recording systems 9, 11, 10, 12 rotate around the patient 14, and so projection measurement data is obtained from different angular directions, which projection measurement data is then used to reconstruct images, for example slice or volume images. If an examination region that is larger than the z-coverage of the detectors 10, 12 is scanned, a sequential scan can be carried out as an alternative to a circular scan without feed, in which sequential scan the patient 14 is moved through the measurement field step-by-step between the individual scans. Spiral scans are likewise carried out for scanning larger examination regions; in these scans, the patient 14 is continuously moved along the system axis 15 and through the measurement field of the recording systems 9, 11, 10, 12 during the circulating scan using X-ray radiation. In a spiral scan, a helical path of the X-ray tubes 9, 10 or the detectors 11, 12 relative to the patient 14 results during the measurement from the motion of the patient 14 along the system axis 15 and the simultaneous revolution of the recording systems 9, 11, 10, 12.

The CT system 3 is controlled by a control and computational unit 6 with computer program code $Prg_1$ to $Prg_n$, available in a program storage medium 7. Acquisition control signals can be transmitted from the control and computational unit 6 via a control interface 16 in order to actuate the CT system 3 as per certain scan protocols.

The projection measurement data (also referred to as raw data below) recorded by the detector 11, 12 is transmitted to the control and computational unit 6 via a raw-data interface 17. This raw data is then processed further in the image reconstruction arrangement 8, possibly after suitable preprocessing. In this example embodiment, the image reconstruction arrangement 8 comprises the program storage medium 7, which stores program code $Prg_1$ to $Prg_n$, that can be executed on a processor of the image reconstruction arrangement 8. The image data reconstructed by the image reconstruction arrangement 8 is then saved in a storage medium 18 of the control and computational unit 6 and/or output in a usual fashion on the monitor 19 of the control and computational unit 6. Said data can also be fed to a network, e.g. a radiology information system (RIS), connected to the CT system 3 via an interface (not illustrated in FIG. 1) and saved on a mass storage medium accessible there or output as images.

The control and computational unit 6 additionally carries out the function of an EKG, with a line 20 being used for transmitting the EKG potentials between patient 14 and control and computational unit 6. In addition, the CT system 3 shown in FIG. 1 also has a contrast-agent instrument 21, by means of which contrast agent 2 can additionally be injected into the blood stream of the patient 14, and so the vessels and the organs of the patient connected thereto, more particularly the chambers of the beating heart 1, are illustrated in the image with a higher contrast. An adjustable amount of contrast agent 2 can thus, in a time controlled fashion, be pumped into a vein of the patient 14 with an adjustable flow speed and in an automated fashion from a storage tank 22 via a contrast-agent tube 23. An electrical connection 24 between the control and computational unit 6 and the contrast-agent instrument 21 allows the parameters of the contrast agent dispensation to be prescribed by the control and computational unit 6. Moreover, this also affords the possibility of carrying out perfusion measurements, for which the proposed method is likewise suitable.

The diffusion of the contrast agent 2 in the body interior is a highly dynamic process. The contrast agent 2 introduced into the patient 14 passes through the bloodstream and only reaches the examination region after a certain amount of time. When the examination region is reached, the concentration of the contrast agent 2 then first of all increases sharply, passes through a maximum, and subsequently falls off again. Therefore, if contrast agent 2 is used during an examination, the time profile of the contrast-agent concentration in the examination object 1 first of all needs to be established within the scope of a preliminary examination in the run up to the examination so that the scan is carried out at a time at which the concentration, and hence the contrast generated in the image, is at a maximum.

In the case of examination objects 1, or parts thereof, subjected to or influenced by cyclical motion, the acquisition of measurement data must moreover be synchronized with a motion signal 4 in order to avoid motion artifacts in the reconstructed image.

Hereinbelow, the method according to an embodiment of the invention will be described with the aid of the heart 1 as examination object. It goes without saying that this method can also be used for the lung, parts of these examination objects, and also for examination regions that are merely influenced by a cyclical motion.

In particular, a particular difficulty lies in identifying the scanning times $T_1$, $T_2$ (shown in FIG. 2) within a cardiac cycle $T_{RR}$, at which scanning times the motion of the heart 1 is minimal or the heart 1 is in a systolic or diastolic rest phase.

Both items of information, the information relating to the time profile of the contrast-agent concentration for identifying a start time for scanning the heart 1 and the information relating to the time profile of the intensity of the heart motion for identifying the systolic or diastolic rest phase, are established in a preliminary examination, the procedure of which is predefined by a preliminary examination protocol stored on the control and computational unit 6.

The following listed items of information (not comprehensive) are stored in the preliminary examination protocol in the form of scanning parameters:

Scanning position: The scanning position at which the preliminary examination is carried out, preferably in the upper cardiac region of the ascending aorta.

Sequence of recording times: The recording times $S_1$-$S_8$ are specified in relation to the cardiac cycle duration $T_{RR}$ and are arranged distributed evenly over the entire range of the cardiac cycle for scanning different phases $P_1$-$P_8$ of the motion between 0% and 100%, with the sequence being selected such that at each time the recording times $S_1$-$S_8$ are arranged as equidistantly as possible from one another in the cardiac cycle. The sequence can for example be calculated by means of a so-called van der Corput sequence according to the following prescription:

$$S(K) = \text{modulus}(100 - 100 * V_2(K), 100), \text{ where}$$

$V_2$=van der Corput sequence with base 2,
K=number of recording times,
S=sequence of the recording times $S_1$-$S_K$ in percent related to a cardiac cycle duration $T_{RR}$.

By way of example, sequences for K=8 and K=15 are as follows:

S(8)=[0, 50, 75, 25, 87.5, 37.5, 62.5, 12.5]
S(15)=[0, 50, 75, 25, 87.5, 37.5, 62.5, 12.5, 93.75, 43.75, 68.75, 18.75, 81.25, 31.25, 56.25]

In particular, the advantage obtained by such a sequence is that measurement data from equidistantly spaced phases $P_1$-$P_8$ is available in all cases in the total number of required scans, which varies strongly between preliminary examinations.

ROI: The ROI represents the region of the image within a slice image, within which image data or attenuation values are measured for establishing the dynamics of the contrast agent 2.

Figure 2:
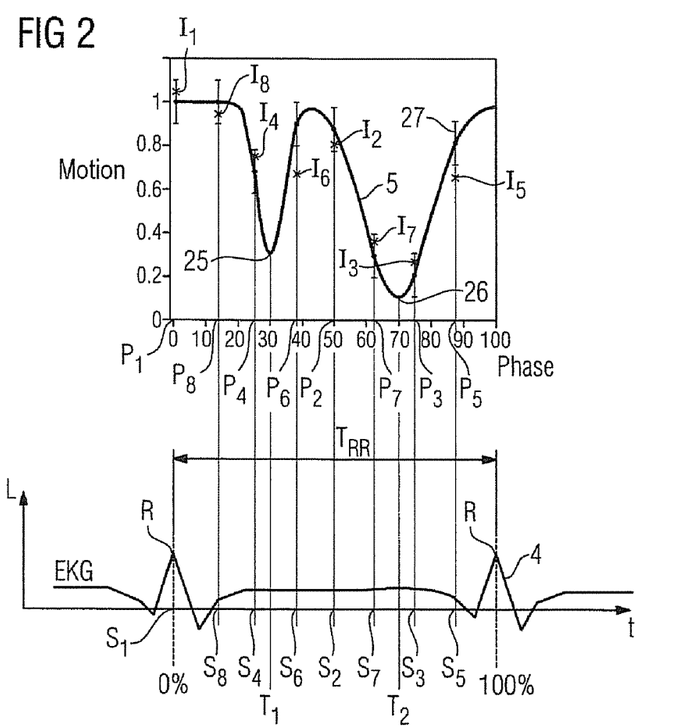
FIG. 2 shows an EKG signal and a profile of a motion curve of a model function corresponding thereto.

In the lower region, FIG. 2 shows a motion signal 4 in the form of an EKG signal and above it, as a result of an approximation, a motion curve 5, which represents a time profile of the intensity of the cardiac motion.

The level of an EKG signal 4 is plotted over time t. The EKG signal 4 illustrates the periodic motion of the heart 1 of the patient 14, wherein the start of a cardiac cycle is determined in each case by an R-wave R, and the duration of the respective cardiac cycle is determined by the RR-interval $T_{RR}$, that is to say by the spacing between the R-wave R starting the respective cardiac cycle and the R-wave R starting the subsequent cardiac cycle. One cardiac phase starts at 0% at an R-wave R and finishes at 100% at the next R-wave R. Conversion between the dimension of time, as plotted in the case of the EKG signal 4, and the cardiac phase, as plotted in the case of the motion curve 5, is possible at all times.

Recording times are denoted by $S_i$, wherein the running index i assumes values between 1 and 8 and characterizes the cardiac cycle by scanning at the appropriate recording time. Although this means that measurement data is recorded at only one recording time in each cardiac cycle, the entire sequence of a total of eight recording times $S_1$-$S_8$ has been plotted so as to clarify scanning at different phases $P_1$-$P_8$. A registered R-wave is used to trigger the recording times $S_1$-$S_8$. Thus, the recording times $S_1$-$S_8$ represent time intervals according to which the scan is started in a delayed fashion, measured from the R-wave. Triggering should take place such that a pause of at least 0.8 seconds is present between two successive scans. Compared to a fixed spacing of one second, the time variation of the scan pulses caused by synchronizing the scan with the EKG signal 4 has no significant influence on evaluating the contrast-agent flow. The first recording time $S_1$ is carried out for the phase $P_1$ at 0%, that is to say directly with the registered R-wave. The maximum intensity of the cardiac motion 1 is expected here.

The motion measured values established at the recording times $S_1$-$S_8$ correspond to intensities of the cardiac motion and are denoted by $I_1$-$I_8$ in the upper diagram in FIG. 2. The motion curve 5 is also plotted, which is determined on the basis of the measured motion measured values $I_1$-$I_8$.

The motion measured values $I_1$-$I_8$ are calculated as follows: So much measurement data is collected at each recording time $S_1$-$S_8$ that a total of two images with a small time offset, e.g. with a spacing of 25 ms, can be reconstructed. In the process, the difference between the two images is a measure of the motion of the heart 1. In order to form the difference, the absolute values of the differences from corresponding pixels in the two images are summed. This summed value is subsequently divided by the total number of pixels in the image or by the summands and thus specifies an average of the image data deviation per pixel. It goes without saying that the difference image can take into account not only the entire image, but also only an image section relevant to the motion acquisition. The lower bound for the average is zero in the case of completely identical images. An upper bound depends on the actually measured cardiac motion or on the phase $P_1$-$P_8$ of the cardiac motion at the recording time $S_1$-$S_8$ and is also influenced by the position of the scanning position in the z-direction in respect of the heart 1. Averages between 40 HU (Hounsfield Units) and 60 HU are typically expected for strong cardiac motion. The calculated averages are normalized with respect to the average of the phase $P_1$ at 0%, since that is where there is the maximum motion and hence the maximum average. The average values normalized thus correspond to the motion measured values $I_1$-$I_8$ used to determine the motion curve 5. Hence, the measured intensity values assume values between 0 and 1.

The number of recording times and hence the number of nodes for determining the motion curve 5 can possibly be very small in the case of very early full contrast. It is thus expedient to include a priori knowledge relating to the profile of the intensity of the cardiac motion and relating to sensible selection of the recording times $S_1$-$S_8$ for scanning different phases $P_1$-$P_8$, such that useable results are also obtained for e.g. fewer than five recording times.

The optimum scanning times $T_1$, $T_2$ or the optimum phases for scanning the heart in a subsequent main examination are determined with the aid of a chi-square fit based on the least-squares method. The fit is based on a model function as an initial motion curve that describes the expected time profile of the intensities of the motion. The model function has two minima, namely the systolic minimum 25 and the diastolic minimum 26. As a default setting, the systolic minimum 25 is set at 30% phase and the diastolic minimum 26 is set at 70% phase.

Figure 3:
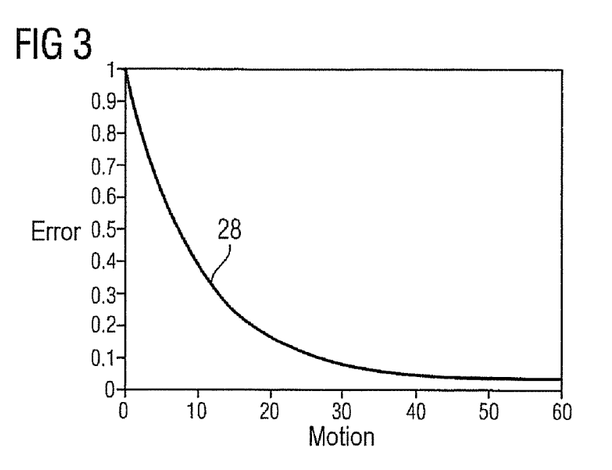
FIG. 3 shows an error function for the motion measured values.

The fit procedure is an approximation method, in which a fit curve, starting from the model function, is approximated to the measured motion measured values $I_1$-$I_8$ with the smallest possible error. The error 27 of the theoretical motion measured values is artificially set to 0.1. The upper diagram in FIG. 2 illustrates these circumstances. Now, in order to stop a measurement series at a wrong z-position (at which no motion is visible) leading to completely random results in respect of the established rest phases or scanning times $T_1$ and $T_2$, a measurement error based on the measured motion at 0% phase is assigned to the motion measured values $I_1$-$I_8$. FIG. 3 plots a corresponding error function 28. The chi-square fit is now carried out on the basis of the theoretical motion measured values of the model function and the measured motion measured values $I_1$-$I_8$. The result of the approximation is that the fit curve results as motion curve 5, from which fit curve the systolic and diastolic rest phases 25, 26 together with the significance values can be established.

It should be mentioned that instead of the CT scanner 3 in the form of a computed tomography scanner described here, it goes without saying that a C-arm scanner can also be used.

In conclusion, the following statements can be made:

An embodiment of the invention relates to a method for scanning a cyclically moved examination object 1 using a contrast agent 2 within the scope of a preliminary examination by way of a CT scanner 3, in which measurement data is recorded at a sequence of recording times $S_1$-$S_8$, and in which a first image is reconstructed at every recording time $S_1$-$S_8$ from the measurement data, from which a time profile of a concentration of the contrast agent 2 is established. An embodiment of the invention is distinguished by virtue of the fact that the recording times $S_1$-$S_8$ for respectively recording a certain phase $P_1$-$P_8$ of the motion are synchronized with a motion signal 4 from the examination object 1, wherein a second image with a small time offset with respect to the first image is reconstructed from the measurement data at each recording time $S_1$-$S_8$, and wherein a motion curve 5 representing a time profile of an intensity of the cyclical motion is established by comparing the first image and the second image at each recording time $S_1$-$S_8$. The particular advantage of this is that motion information can also be obtained from the mandatory preliminary examination with a minimally increased dose. An embodiment of the invention moreover relates to a corresponding CT scanner 3 and a computer program.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for scanning a cyclically movable examination object using a contrast agent within the scope of a preliminary examination by way of a computer tomography (CT) scanner, in which a first image is reconstructable at one of a plurality of discrete recording times from measurement data, from which a time profile of a concentration of the contrast agent is established, the method comprising:
    synchronizing the plurality of discrete recording times for respectively recording a phase of a cyclical motion with a motion signal from the examination object;
    scanning the measurement data at each of the plurality of discrete recording times, each of the plurality of discrete recording times being associated with a different cycle;
    reconstructing a second image, with a time offset with respect to the first image, from the measurement data at each of the plurality of discrete recording times, the time offset being smaller than a time difference between two consecutive recording times;
    establishing a motion curve, representing a time profile of an intensity of the cyclical motion, by comparing the first image and the second image at each of the plurality of discrete recording times; and
    scanning the cyclically movable examination object in a subsequent main scan using at least one scanning time corresponding to at least one local minimum determined based on the established motion curve.

2. The method as claimed in claim 1, further comprising:
    selecting the plurality of the discrete recording times such that an even distribution of the recorded phases are achieved over a motion cycle at every observed time.

3. The method as claimed in claim 1, further comprising:
    determining the plurality discrete of recording times from a van der Corput sequence with base two.

4. The method as claimed in claim 1, wherein the establishing the motion curve includes establishing a motion value as a measure of the intensity of the cyclical motion at each of the plurality of discrete recording times from a difference between the corresponding one of the first image and the corresponding one of the second image.

5. The method as claimed in claim 4, wherein the establishing the motion curve establishes the motion curve by approximating a model function to the established motion measured values at the plurality of discrete recording times.

6. The method as claimed in claim 5, wherein the approximating uses a chi-square fit based on the least-squares method.

7. The method as claimed in claim 1, wherein the at least one scanning time corresponds to little motion of the examination object.

8. The method as claimed in claim 7, further comprising:
    establishing a significance value for the at least one scanning time, the significance value representing a measure of the probability of the at least one local minimum occurring.

9. The method as claimed in claim 1, wherein the examination object is at least one of a heart and a lung, and
    the motion signal is at least one of an electrocardiogram (EKG) signal and a respiratory signal.

10. A computer tomography (CT) scanner for scanning a cyclically movable examination object using a contrast agent within the scope of a preliminary examination, in which a first image is reconstructable at a plurality of discrete recording times from measurement data, from which a time profile of a concentration of the contrast agent is established, the CT scanner comprising:

a processor configured to,
- synchronize the plurality of discrete recording times for respectively recording a phase of a cyclical motion with a motion signal from the examination object;
- scan the measurement data at each of the plurality of discrete recording times, each of the plurality of discrete recording times being associated with a different cycle;
- reconstruct a second image, with a time offset with respect to the first image, from the measurement data at each of the plurality of discrete recording times, the time offset being smaller than a time difference between two consecutive recording times;
- establish a motion curve, representing a time profile of an intensity of the cyclical motion, by comparing the first image and the second image at each of the plurality of discrete recording times; and
- scan the cyclically movable examination object in a subsequent main scan using at least one scanning time corresponding to at least one local minimum determined based on the established motion curve.

11. The method as claimed in claim 2, wherein the selecting the plurality of discrete recording times includes determining the plurality of discrete recording times from a van der Corput sequence with base two.

12. A non-transitory computer readable medium including a computer program product, the computer program product comprising instructions which, when executed by a processor, cause the processor to implement the method of claim 1.

13. The method as claimed in claim 1, wherein the plurality of discrete recording times are discontinuous.

* * * * *